(12) United States Patent
Grass et al.

(10) Patent No.: US 7,361,714 B2
(45) Date of Patent: Apr. 22, 2008

(54) CATALYST AND METHOD FOR HYDROGENATING AROMATIC COMPOUNDS

(75) Inventors: Michael Grass, Haltern am See (DE); Alfred Kaizik, Marl (DE); Wilfried Bueschken, Haltern am See (DE); Axel Tuchlenski, Weinheim (DE); Dietrich Maschmeyer, Recklinghausen (DE); Kurt-Alfred Gaudschun, Recklinghausen (DE); Frank Brocksien, Duelmen (DE)

(73) Assignee: OXENO Olefinchemie GmbH, Marl (DE)

( * ) Notice: Subject to any disclaimer, the term of this patent is extended or adjusted under 35 U.S.C. 154(b) by 314 days.

(21) Appl. No.: 10/511,595

(22) PCT Filed: Apr. 26, 2003

(86) PCT No.: PCT/EP03/04386

§ 371 (c)(1),
(2), (4) Date: Nov. 2, 2004

(87) PCT Pub. No.: WO03/103830

PCT Pub. Date: Dec. 18, 2003

(65) Prior Publication Data

US 2006/0183936 A1    Aug. 17, 2006

(30) Foreign Application Priority Data

Jun. 10, 2002   (DE) .................... 102 25 565

(51) Int. Cl.
C08C 19/02 (2006.01)

(52) U.S. Cl. .................. 525/338; 502/80; 502/84; 502/103; 502/104; 560/127

(58) Field of Classification Search .............. 502/80, 502/84, 103, 104; 560/127; 525/338
See application file for complete search history.

(56) References Cited

U.S. PATENT DOCUMENTS

| | | | |
|---|---|---|---|
| 3,636,108 A | 1/1972 | Brake | |
| 4,079,092 A * | 3/1978 | Hayes et al. ............ | 585/268 |
| 5,202,475 A | 4/1993 | Cook et al. | |
| 5,578,546 A | 11/1996 | Maschmeyer et al. | |
| 6,015,928 A | 1/2000 | Gubisch et al. | |
| 6,184,424 B1 | 2/2001 | Bueschken et al. | |
| 6,239,318 B1 | 5/2001 | Schuler et al. | |
| 6,284,917 B1 * | 9/2001 | Brunner et al. ............ | 560/127 |
| 6,331,657 B1 | 12/2001 | Kaizik et al. | |
| 6,350,820 B1 * | 2/2002 | Hahnfeld et al. ........ | 525/332.9 |
| 6,403,836 B2 | 6/2002 | Kaizik et al. | |
| 6,407,295 B1 | 6/2002 | Kaizik et al. | |
| 6,482,992 B2 | 11/2002 | Scholz et al. | |
| 6,492,564 B1 | 12/2002 | Wiese et al. | |
| 6,500,991 B2 | 12/2002 | Wiese et al. | |
| 6,555,716 B2 | 4/2003 | Protzmann et al. | |
| 6,570,033 B2 | 5/2003 | Rottger et al. | |
| 6,627,782 B2 | 9/2003 | Kaizik et al. | |
| 6,680,414 B2 | 1/2004 | Knoop et al. | |
| 6,720,457 B2 | 4/2004 | Drees et al. | |
| 6,818,770 B2 | 11/2004 | Selent et al. | |
| 6,924,389 B2 | 8/2005 | Jackstell et al. | |
| 6,956,133 B2 | 10/2005 | Jackstell et al. | |
| 6,960,699 B2 | 11/2005 | Totsch et al. | |
| 7,009,068 B2 | 3/2006 | Schmutzler et al. | |
| 7,109,346 B2 | 9/2006 | Beller et al. | |
| 2004/0097773 A1 | 5/2004 | Beckmann et al. | |
| 2004/0236133 A1 | 11/2004 | Selent et al. | |
| 2004/0238787 A1 | 12/2004 | Wiese et al. | |
| 2004/0242947 A1 | 12/2004 | Beller et al. | |
| 2004/0260113 A1 | 12/2004 | Bueschken et al. | |
| 2005/0038285 A1 | 2/2005 | Maschmeyer et al. | |
| 2005/0043279 A1 | 2/2005 | Selent et al. | |
| 2005/0101800 A1 | 5/2005 | Bueschken et al. | |
| 2005/0182277 A1 | 8/2005 | Totsch et al. | |
| 2005/0209489 A1 | 9/2005 | Moller et al. | |
| 2005/0234270 A1 | 10/2005 | Kaizik et al. | |
| 2005/0256281 A1 | 11/2005 | Grund et al. | |
| 2006/0036121 A1 | 2/2006 | Kaizik et al. | |
| 2006/0128998 A1 | 6/2006 | Lueken et al. | |
| 2006/0129004 A1 | 6/2006 | Lueken et al. | |
| 2006/0161017 A1 | 7/2006 | Grass et al. | |
| 2006/0241324 A1 | 10/2006 | Moeller et al. | |

FOREIGN PATENT DOCUMENTS

| | | |
|---|---|---|
| DE | 29 09 663 | 9/1979 |
| DE | 100 54 347 | 5/2002 |
| EP | 0 067 058 | 12/1982 |
| EP | 0 324 984 | 7/1989 |
| WO | 98 57913 | 12/1998 |
| WO | 99 32427 | 7/1999 |
| WO | 00 78704 | 12/2000 |

* cited by examiner

Primary Examiner—Ling-Sui Choi
(74) Attorney, Agent, or Firm—Oblon, Spivak, McClelland, Maier & Neustadt, P.C.

(57) ABSTRACT

The invention relates to the hydrogenation of aromatic compounds, in particular the preparation of alicyclic polycarboxylic acids or esters of these, via ring hydrogenation of the corresponding aromatic polycarboxylic acids or esters of these, and also to catalysts suitable for this purpose.

20 Claims, No Drawings

CATALYST AND METHOD FOR HYDROGENATING AROMATIC COMPOUNDS

CROSS REFERENCES TO RELATED APPLICATIONS

This application is a national stage application of International Patent Application No. PCT/EP03/04386, filed on Apr. 26, 2003, and claims priority to German Patent Application No. 102 25 565.2, filed on Jun. 10, 2002, both of which are incorporated herein by reference in their entireties.

The invention relates to the hydrogenation of aromatic compounds, in particular the preparation of alicyclic polycarboxylic acids or esters of these, by ring hydrogenation of the corresponding aromatic polycarboxylic acids or esters of these, and also to catalysts suitable for this purpose.

Alicyclic polycarboxylic esters, such as the esters of cyclohexane-1,2-dicarboxylic acid, are used as a component of lubricating oil and as auxiliaries in metalworking. They are also used as plasticizers for polyolefins and for PVC.

For plasticizing PVC it is currently mainly esters of phthalic acid that are used, for example dibutyl, dioctyl, dinonyl, or didecyl esters. Recently, there has been increasing controversy about the use of these phthalates, and therefore there is a risk that their use in plastics could become restricted. Alicyclic polycarboxylic esters, some of which have been described in the literature as plasticizers for plastics, could then be available as suitable replacements.

The most economic route to preparation of alicyclic polycarboxylic esters in most cases is ring hydrogenation of the corresponding aromatic polycarboxylic esters, for example of the abovementioned phthalates. Some processes for this purpose have been disclosed:

U.S. Pat. No. 5,286,898 and U.S. Pat. No. 5,319,129 describe a process which can hydrogenate dimethyl terephthalate on supported Pd catalysts doped with Ni or with Pt and/or with Ru, at temperatures of 140° C. or above and at a pressure of from 50 to 170 bar, to give the corresponding dimethyl hexahydroterephthalate.

U.S. Pat. No. 3,027,398 discloses the hydrogenation of dimethyl terephthalate on supported Ru catalysts from 110 to 140° C. and from 35 to 105 bar.

DE 28 23 165 hydrogenates aromatic carboxylic esters on supported Ni, Ru, Rh, and/or Pd catalysts, to give the corresponding alicyclic carboxylic esters at from 70 to 250° C. and from 30 to 200 bar. A macroporous support is used here, with an average pore size of 70 nm and a BET surface area of about 30 $m^2/g$.

WO 99/32427 and WO 00/78704 disclose processes for hydrogenating benzenepolycarboxylic esters to give the corresponding alicyclic compounds. Here, use is made of supported catalysts which comprise a metal of the 8th transition group alone or together with at least one metal of the 1st or 7th transition group of the periodic table, and which have macropores. Ruthenium is used as the preferred metal of the 8th transition group. For the hydrogenation, use is made of three different types of catalyst which differ substantially in their average pore diameter and their BET surface areas.

Catalyst I: average pore diameter greater than 50 nm and BET surface area smaller than 30 $m^2/g$ Catalyst II: average pore diameter from 5 to 20 nm and BET surface area greater than 50 $m^2$ μg Catalyst III: average pore diameter greater than 100 nm and BET surface area smaller than 15 $m^2/g$ The catalysts used for ring-hydrogenating aromatic carboxylic acids or esters of these are intended to permit a high reaction rate, generate only a small proportion of by-products, and have a long operating time.

The activity and selectivity of hydrogenation catalysts depend on their surface properties, such as pore size, BET surface area, or surface concentration of the active metals.

In a continuously operated process, a catalyst is then exposed to mechanical, thermal, and chemical stresses which alter the pore size or the BET surface area and therefore reduce the activity and selectivity of this catalyst.

For example, many catalysts are found to exhibit not only mechanical abrasion but also enlargement of pore volumes and diameter through acid etching.

Aromatic polycarboxylic esters often comprise small amounts of carboxylic acids, and traces of acid are also produced during the ring hydrogenation of esters. Partial esters of polycarboxylic acids, or polycarboxylic acids themselves, are acidic by virtue of their structure. This means that a hydrogenation catalyst suitable for a continuous process should be resistant to acid under the conditions of hydrogenation, even at relatively high temperatures.

The known catalysts do not yet fulfill the desired requirements in relation to activity, selectivity, or stability. For example, it is known that, unlike $\alpha$-$Al_2O_3$, $\gamma$-$Al_2O_3$ is insufficiently resistant to acid.

An object was therefore to develop the catalysts for ring-hydrogenating aromatic carboxylic acids and/or esters of these, with improved property profiles.

Surprisingly, it has now been found that catalysts which comprise at least one metal of the eighth transition group and are composed of a support material with an average pore diameter of from 25 to 50 nm and with a specific surface area greater than 30 $m^2/g$ hydrogenate aromatic carboxylic acids and/or esters of these (full esters or partial esters) with high selectivity and space-time yield to give the corresponding alicyclic polycarboxylic acids or esters of these, without significant side reactions.

The present invention therefore provides a catalyst for hydrogenating aromatic compounds to give the corresponding alicyclic compounds, which comprises at least one metal of the eighth transition group of the periodic table on or in a support material, where the support material has an average pore diameter of from 25 to 50 nm and a specific surface area greater than 30 $m^2/g$.

Catalysts of this type may in particular be used for hydrogenating aromatic compounds. The present invention also provides a process for catalytically hydrogenating aromatic compounds, using hydrogen-containing gases on a catalyst which comprises at least one metal of the eighth transition group of the periodic table on or in a support material, where the support material has an average pore diameter of from 25 to 50 nm and a specific surface area greater than 30 $m^2/g$.

In principle, the catalysts may comprise any of the metals of the eighth transition group of the periodic table. The active metals preferably used are platinum, rhodium, palladium, cobalt, nickel, or ruthenium, or a mixture of two or more of these, and ruthenium in particular is used here as active metal.

Besides the abovementioned metals, there may be at least one metal of the first and/or seventh transition group of the periodic table of the elements present in the catalysts. It is preferable to use rhenium and/or copper.

The content of the active metals, i.e. of the metals of the first and/or seventh and/or eighth transition group, is generally from 0.1 to 30% by weight. The precious metal content, i.e. content of the metals of the eighth transition group (more specifically: of the fifth and sixth period), calculated in terms of metal, in the range from 0.1 to 10% by weight, in particular in the range from 0.8 to 5% by weight, very particularly from 1 to 3% by weight.

To prepare the catalyst of the invention, use is made of support materials with an average pore diameter in the range from 25 to 50 nm (the average pore diameter is determined by Hg porosimetry, in particular to DIN 66133.)

In the support materials used a distinction may be made between micropores (pore diameter smaller than 2 nm), mesopores (pore diameter from 2 to 50 nm), and macropores (pore diameter greater than 50 nm). For instance, it is possible to use support materials with the following combinations of pore type.
a) only mesopores
b) micropores and mesopores
c) mesopores and macropores
d) micropores and mesopores, and macropores
e) micropores and macropores A decisive factor for preparing the catalyst of the invention is that, irrespective of the pore size distribution, the average pore diameter of the support material is from 25 to 50 nm. The average pore diameter is preferably from 25 to 40 nm, very particularly preferably from 30 to 40 nm.

It is therefore also possible to use support materials with high macropore content (>550%) as long as the average pore diameter is from 25 to 50 nm, preferably from 25 to 40 nm, very particularly preferably from 30 to 40 nm.

The specific surface area of the support (determined by the BET method by nitrogen adsorption to DIN 66131 is greater than 30 $m^2$ g, and the specific surface area is preferably from 30 to 90 $m^2/g$ or from 35 to 90 $m^2/g$, in particular from 40 to 60 $m^2/g$.

In one specific embodiment of the invention, the support materials used to prepare the catalysts comprise those in which over 90%, in particular over 95%, of the total pore volume is made up by micro- and mesopores, i.e. by pores with a diameter of from 0.1 to 50 nm, preferably from 0.1 to 20 nm.

The supports used for preparing the catalysts of the invention comprise solids whose average pore diameter and whose specific surface area lie within the ranges mentioned. Examples of substances which may be used as support are the following: activated carbon, silicon carbide, aluminum oxide, silicon oxide, aluminosilicate, titanium dioxide, zirconium dioxide, magnesium oxide, and/or zinc oxide, or a mixture of these.

To prepare the catalysts of the invention it is preferable to use supports which are resistant to carboxylic acids under the conditions of hydrogenation. Examples of these are activated carbon, silicon carbide, silicon dioxide, titanium dioxide, and/or zirconium dioxide, and mixtures of these compounds.

The support materials used very particularly preferably comprise titanium dioxides. Titanium dioxide occurs in three forms (anatase, rutile, brookite), of which anatase and rutile are the commonest. To prepare the catalysts of the invention, use may be made of any of the forms of titanium dioxide, or titanium dioxides in which at least two forms are present alongside one another, or a mixture of various titanium dioxides, if their average pore diameter and specific surface area are within the range of the invention. A preferred support material is Aerolyst 7711® (product marketed by Degussa AG, Düsseldorf, Germany). This support is composed of from 15 to 20% by weight of rutile and from 80 to 85% by weight of anatase. Examples of other titanium dioxide supports which are suitable for preparing the catalysts of the invention are supports prepared from titanium oxides from a sulfuric acid process. They generally comprise >98% of anatase.

The catalysts of the invention may be obtained by applying at least one metal of the eighth transition group of the periodic table and, where appropriate, at least one metal of the first and/or seventh transition group of the periodic table, to a suitable support. It is also possible for the active metals and the support to be prepared simultaneously, i.e. it is possible to use a bulk catalyst.

The application method may be impregnation of the support in aqueous metal salt solutions, e.g. aqueous ruthenium salt solutions, spray-application of appropriate metal salt solutions onto the support, or any other suitable method. Suitable metal salts of the first, seventh, or eighth transition group of the periodic table are the nitrates, nitrosyl nitrates, halides, carbonates, carboxylates, acetylacetonates, chloro complexes, nitrito complexes, or amine complexes of the appropriate metals, preference being given to the nitrates and nitrosyl nitrates.

In the case of catalysts which comprise not only the metal of the eighth transition group of the periodic table but also other metals applied as active metal, the metal salts or metal salt solutions may be applied simultaneously or in succession.

The supports impregnated or coated with metal salt solution are then dried, preferably at temperatures of from 80 to 150° C., and optionally calcined at temperatures of from 200 to 600° C. In the event of separate impregnation application, the catalyst is dried after each impregnation step and optionally calcined, as described above. There is no restriction here on the sequence in which the active components are applied.

The application of the active component(s), drying, and calcination may optionally take place in a single operation, for example by spray-application of an aqueous metal salt solution to the support at temperatures above 200° C.

It is essential that the catalysts of the invention are converted to a form which has low flow-resistance during the hydrogenation process, examples being tablets, cylinders, extrudates, and rings. Various points in the catalyst preparation process here may be chosen for the shaping process.

In the process of the invention, the hydrogenation is carried out in the liquid phase or gas phase. The hydrogenation may be carried out batchwise or continuously on suspended catalysts or particulate catalysts in a fixed bed. In the process of the invention preference is given to continuous hydrogenation on a fixed-bed arrangement of catalysts where the product/starting material phase is primarily in the liquid state under the conditions of the reaction.

If the hydrogenation is carried out continuously on a catalyst arranged in a fixed bed, it is advantageous to convert the catalyst into the active form prior to the hydrogenation. This may be achieved by reduction of the catalyst using hydrogen-containing gases, following a temperature program. This reduction may, where appropriate, be carried out in the presence of a liquid phase which trickles over the catalyst. The liquid phase used here may comprise a solvent or the hydrogenation product.

Differing versions of the process of the invention may be selected. It can be carried out adiabatically, polytropically, or practically isothermally, i.e. with a temperature rise typically smaller than 10° C., in one or more stages. In the latter case it is possible to operate all of the reactors, advantageously tubular reactors, adiabatically or practically isothermally, or else to operate one or more adiabatically and the others practically isothermally. It is also possible to hydrogenate the aromatic compounds in a straight pass or with product return.

The process of the invention is carried out in the mixed liquid/gas phase or liquid phase, cocurrently in three-phase reactors, the hydrogenation gas being distributed in a manner known per se within the liquid starting material/product stream. To promote uniform liquid distribution, improved dissipation of the heat of reaction, and high space-time yield, the reactors are preferably operated with high liquid flow rates of from 15 to 120, in particular from 25 to 80, m³ per m² of cross section of the empty reactor per hour. If the reactor is operated with a straight pass, the liquid hourly space velocity (LHSV) over the catalyst may be from 0.1 to 10 h⁻¹.

The hydrogenation may be carried out in the absence, or preferably in the presence, of a solvent. Solvents which may be used are any of the liquids which form a homogeneous solution with the starting material and product, exhibit inert behavior under hydrogenation conditions, and are easy to remove from the product. The solvent may also be a mixture of two or more substances and, where appropriate, comprise water.

Examples of substances which may be used as solvents are the following: straight-chain or cyclic ethers, such as tetrahydrofuran or dioxane, and also aliphatic alcohols whose alkyl radical has from 1 to 13 carbon atoms.

Examples of alcohols which may preferably be used are isopropanol, n-butanol, isobutanol, n-pentanol, 2-ethylhexanol, nonanols, industrial nonanol mixtures, decanol, and industrial decanol mixtures, and tridecanols.

If alcohols are used as solvent it can be advantageous to use the alcohol or alcohol mixture which would be produced during saponification of the product. This prevents any by-product formation via transesterification. Another preferred solvent is the hydrogenation product itself.

By using a solvent it is possible to limit the concentration of aromatic compounds in the reactor feed, and the result can be better temperature control achieved in the reactor. This can minimize side-reactions and therefore increase product yield. The content of aromatic compounds in the reactor feed is preferably from 1 to 35%, in particular from 5 to 25%. In the case of reactors operated in loop mode, the desired concentration range can be adjusted via the circulation rate (quantitative ratio of returned hydrogenation discharge to starting material).

The process of the invention is carried out in the pressure range from 3 to 300 bar, in particular from 15 to 200 bar, very particularly from 50 to 200 bar. The hydrogenation temperatures are from 50 to 250° C., in particular from 100 to 200° C.

Hydrogenation gases which may be used are any desired hydrogen-containing gas mixtures in which there are no detrimental amounts present of catalyst poisons, such as carbon monoxide or hydrogen sulfide. The use of inert gases is optional, and is preferable to use hydrogen of purity greater than 95%, in particular greater than 98%. Examples of the inert gas constituents are nitrogen and methane.

Each of the reactors may be supplied with fresh hydrogen. However, in order to reduce hydrogen consumption and the discharge losses associated with the exhaust gas, it is advantageous to use the exhaust gas from one reactor as hydrogenation gas for another reactor. For example, in a process carried out in two reactors arranged in series it is advantageous to feed fresh hydrogen into the second reactor and to pass the exhaust gas from the second reactor into the first reactor. In this instance, starting material and hydrogenation gas flow in countercurrent through the reactors. It is advantageous for the excess of hydrogen, based on the stoichiometric amount needed, to be kept below 30%, in particular below 10%, very particularly below 5%.

If nonyl phthalates or mixtures of nonyl phthalates are converted to the corresponding 1,2-cyclohexanedicarboxylic esters, the hydrogenation is preferably carried out in the mixed liquid/gas phase or the liquid phase in two reactors arranged in series. The first reactor here is operated in loop mode, i.e. some of the hydrogenation discharged from the first reactor is passed together with fresh starting material to the head of the first reactor. The rest of the discharge from the first reactor is passed straight to a second reactor for hydrogenation. It is also possible to use two or more relatively small loop reactors instead of a large loop reactor, these being in a series or parallel arrangement. It is also possible to operate two or more reactors arranged in series or in parallel with one another instead of a large straight-pass reactor. However, it is preferable to use only one loop reactor and only one straight-pass reactor.

The process of the invention is preferably carried out under the following conditions:

The concentration of the starting material in the feed of the first reactor (loop reactor) is from 5 to 30% by weight, in particular from 8 to 15% by weight.

The concentration of the starting material in the hydrogenation discharge from the first reactor is from 0.3 to 8% by weight, in particular from 1.5 to 4% by weight.

The liquid hourly space velocity over the catalyst (LHSV, liters of fresh starting material per liter of catalyst per hour) in the loop reactor is from 0.1 to 5 h⁻¹, in particular from 0.5 to 3 h⁻¹.

The surface area loading in the loop reactor is in the range from 25 to 140 m³/m²/h, in particular in the range from 50 to 90 m³/m²/h.

The average hydrogenation temperatures in the loop reactor are from 70 to 150° C., in particular from 80 to 120° C.

The hydrogenation pressure in the loop reactor is from 25 to 200 bar, in particular from 80 to 100 bar.

The concentration of starting material in the starting material for the second reactor is smaller than 0.3% by weight, in particular smaller than 0.1% by weight, very particularly smaller than 0.05% by weight.

The liquid hourly space velocity in the second reactor (liters of nonyl phthalate per liter of catalyst per hour) is from 1 to 8 h⁻¹, in particular from 2 to 5 h⁻¹.

The average temperature in the second reactor is from 70 to 150° C., in particular from 80 to 120° C.

The hydrogenation pressure in the second reactor is from 25 to 200 bar, in particular from 80 to 100 bar.

The versions of the process are particularly suitable for hydrogenating phthalic esters, especially for nonyl phthalates (in the form of "isononyl phthalate" isomer mixture, e.g. VESTINOL 9 from OXENO GmbH).

The process of the invention can convert aromatic compounds, such as polycarboxylic acids and/or monocarboxylic acids or derivatives of these, in particular their alkyl esters, to the corresponding alicyclic polycarboxylic compounds. Either full esters or partial esters can be hydrogenated here. Full esters are compounds in which all of the acid groups have been esterified. Partial esters are compounds having at least one free acid group (or anhydride group) and at least one ester group.

If polycarboxylic esters are used in the process of the invention, these preferably contain 2, 3 or 4 ester functions.

The aromatic compounds or polycarboxylic esters preferably used in the process of the invention are benzenepolycarboxylic, biphenylpolycarboxylic, naphthalenepolycarboxylic, and/or anthracenepolycarboxylic acids, or their anhydrides and/or esters, e.g. alkyl esters having from 2 to 15 carbon atoms. The resultant alicyclic polycarboxylic acids or derivatives of these are composed of one or more $C_6$ rings, where appropriate linked by a C—C bond or fused.

The alcohol component of the aromatic compounds (if those used are carboxylic esters) is preferably composed of branched or unbranched alkyl, cycloalkyl, or alkoxyalkyl groups having from 1 to 25 carbon atoms. These may be identical or different within one molecule of a polycarboxylic ester, i.e. the isomers or chain lengths present in a compound may differ. It is also possible, of course, to use a mixture of isomers with respect to the substitution pattern of the aromatic system, e.g. a mixture of phthalic ester and terephthalic ester.

In one preferred embodiment, the present invention provides a process for the hydrogenation of benzene-1,2-, -1,3-, or -1,4-dicarboxylic esters, and/or of benzene-1,2,3-, -1,3,5-, or -1,2,4-tricarboxylic esters, i.e. the products comprise the isomers of cyclohexane-1,2-, -1,3-, or -1,4-dicarboxylic esters, or of cyclohexane-1,2,3-, -1,3,5-, or -1,2,4-tricarboxylic esters.

Examples of esters which may be used in the process of the invention are those of the following aromatic carboxylic acids:

naphthalene-1,2-dicarboxylic acid, naphthalene-1,3-dicarboxylic acid, naphthalene-1,4-dicarboxylic acid, naphthalene-1,5-dicarboxylic acid, naphthalene-1,6-dicarboxylic acid, naphthalene-1,7-dicarboxylic acid, naphthalene-1,8-dicarboxylic acid, phthalic acid (benzene-1,2-dicarboxylic acid), isophthalic acid (benzene-1,3-dicarboxylic acid), terephthalic acid (benzene-1,4-dicarboxylic acid), benzene-1,2,3-tricarboxylic acid, benzene-1,2,4-tricarboxylic acid (trimellitic acid), benzene-1,3,5-tricarboxylic acid (trimesic acid), benzene-1,2,3,4-tetracarboxylic acid. It is also possible to use acids which are produced from the acids mentioned by using alkyl, cycloalkyl, or alkoxyalkyl groups to substitute one or more of the hydrogen atoms bonded to the aromatic core.

Examples of compounds which may be used are alkyl, cycloalkyl, or alkoxyalkyl esters of the abovementioned acids, these radicals encompassing, independently of one another, from 1 to 25, in particular from 3 to 15, very particularly from 8 to 13, particularly 9, carbon atoms. These radicals may be linear or branched. If a starting material has more than one ester group, these radicals may be identical or different.

Examples of compounds which may be used in the process of the invention as ester of an aromatic polycarboxylic acid are the following:

nmonomethyl terephthalate, dimethyl terephthalate, diethyl terephthalate, di-n-propyl terephthalate, dibutyl terephthalate, diisobutyl terephthalate, di-tert-butyl terephthalate, monoglycol terephthalate, diglycol terephthalate, n-octyl terephthalate, diisooctyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, ditridecyl terephthalate, di-n-octadecyl terephthalate, diisooctadecyl terephthalate, di-n-eicosyl terephthalate, monocyclohexyl terephthalate; monomethyl phthalate, dimethyl phthalate, di-n-propyl phthalate, di-n-butyl phthalate, diisobutyl phthalate, di-tert-butyl phthalate, monoglycol phthalate, diglycol phthalate, di-n-octyl phthalate, diisooctyl phthalate, di-2-ethylhexyl phthalate, di-n-nonyl phthalate, diisononyl phthalate, di-n-decyl phthalate, di-2-propylheptyl phthalate, diisodecyl phthalate, di-n-undecyl phthalate, diisoundecyl phthalate, ditridecyl phthalate, di-n-octadecyl phthalate, diisooctadecyl phthalate, di-n-eicosyl phthalate, monocyclohexyl phthalate, dicyclohexyl phthalate, monomethyl isophthalate, dimethyl isophthalate, diethyl isophthalate, di-n-propyl isophthalate, di-n-butyl isophthalate, diisobutyl isophthalate, di-tert-butyl isophthalate, monoglycol isophthalate, diglycol isophthalate, di-n-octyl isophthalate, diisooctyl isophthalate, 2-ethylhexyl isophthalate, di-n-nonyl isophthalate, diisononyl isophthalate, di-n-decyl isophthalate, diisodecyl isophthalate, di-n-undecyl isophthalate, diisododecyl isophthalate, di-n-dodecyl isophthalate, ditridecyl isophthalate, di-n-octadecyl isophthalate, diisooctadecyl isophthalate, di-n-eicosyl isophthalate, monocyclohexyl isophthalate.

The process of the invention can in principle also be used on benzoic acid and esters thereof. These include not only alkyl benzoates but also benzoates of diols, for example glycol dibenzoate, diethylene glycol benzoate, triethylene glycol dibenzoate, and propylene glycol dibenzoate. Each alcohol component of the alkyl benzoate may be composed of from 1 to 25 carbon atoms, preferably from 8 to 13 carbon atoms, in a linear or branched structure.

It is also possible to use mixtures made from two or more polycarboxylic esters. Examples of mixtures of this type may be obtained in the following ways:

a) a polycarboxylic acid is partially esterified using an alcohol in such a way as to give both full and partial esters.

b) A mixture of at least two polycarboxylic acids is esterified using an alcohol, producing a mixture of at least two full esters.

c) A polycarboxylic acid is treated with an alcohol mixture, and the product can be a corresponding mixture of the full esters.

d) A polycarboxylic acid is partially esterified using an alcohol mixture.

e) A mixture of at least two carboxylic acids is partially esterified using an alcohol mixture.

f) A mixture of at least two polycarboxylic acids is partially esterified using an alcohol mixture.

Instead of the polycarboxylic acids in reactions a) to f), use may also be made of their anhydrides.

Aromatic esters are often prepared industrially from alcohol mixtures, in particular the full esters by route c).

Examples of corresponding alcohol mixtures are:

$C_5$ alcohol mixtures prepared from linear butenes by hydroformylation followed by hydrogenation;

$C_5$ alcohol mixtures prepared from butene mixtures which comprise linear butenes and isobutene, by hydroformylation followed by hydrogenation;

$C_6$ alcohol mixtures prepared from a pentene or from a mixture of two or more pentenes, by hydroformylation followed by hydrogenation;

$C_7$ alcohol mixtures prepared from triethylene or dipropene or from a hexeneisomer or from some other mixture of hexeneisomers, by hydroformylation followed by hydrogenation;

$C_8$ alcohol mixtures, such as 2-ethylhexanol (2 isomers), prepared by aldol condensation of n-butyraldehyde followed by hydrogenation;

$C_9$ alcohol mixtures prepared from $C_4$ olefins by dimerization, hydroformylation, and hydrogenation. The starting materials here for preparing the $C_9$ alcohols may be isobutene or a mixture of linear butenes or mixtures of linear butenes and isobutene. The $C_4$ olefins may be dimerized with the aid of various catalysts, such as protonic acids, zeolites, organometallic nickel compounds, or solid nickel-containing catalysts. The $C_8$ olefin mixtures may be hydroformylated with the aid of rhodium catalysts or cobalt catalysts. There is therefore a wide variety of industrial $C_9$ alcohol mixtures.

$C_{10}$ alcohol mixtures prepared from tripropylene by hydroformylation followed by hydrogenation; 2-propylheptanol (2 isomers) prepared by aldol condensation of valeraldehyde followed by hydrogenation;

$C_{10}$ alcohol mixtures prepared from a mixture of at least two $C_5$ aldehydes by aldol condensation followed by hydrogenation;

$C_{13}$ alcohol mixtures prepared from hexaethylene, tetrapropylene, or tributene, by hydroformylation followed by hydrogenation.

Other alcohol mixtures may be obtained by hydroformylation followed by hydrogenation from olefins or olefin mixtures which arise in Fischer-Tropsch syntheses, in the dehydrogenation of hydrocarbons, in metathesis reactions, in the polygas process, or in other industrial processes, for example.

Olefin mixtures with olefins of differing carbon numbers may also be used to prepare alcohol mixtures.

The process of the invention can use any ester mixture prepared from aromatic polycarboxylic acids and from the abovementioned alcohol mixtures. According to the invention, preference is given to esters prepared from phthalic acid or phthalic anhydride and from a mixture of isomeric alcohols having from 6 to 13 carbon atoms.

Examples of industrial phthalates which can be used in the process of the invention are products with the following trade names:

Vestinol C (Di-n-butyl phthalate) (CAS No. 84-74-2); Vestinol IB (Diisobutyl phthalate) (CAS No. 84-69-5); Jayflex DINP (CAS No. 68515-48-0); Jayflex DIDP (CAS No. 68515-49-1); Palatinol 9-P (68515-45-7), Vestinol 9 (CAS No. 28553-12-0); TOTM (CAS No. 3319-31-1); Linplast 68-TM, Palatinol N (CAS No. 28553-12-0); Jayflex DHP (CAS No. 68515-50-4); Jayflex DIOP (CAS No. 27554-26-3); Jayflex UDP (CAS No. 68515-47-9); Jayflex DIUP (CAS No. 85507-79-5); Jayflex DTDP (CAS No. 68515-47-9); Jayflex L9P (CAS NO. 68515-45-7); Jayflex L911P (CAS No. 68515-43-5); Jayflex L11P (CAS No. 3648-20-2); Witamol 110 (CAS No. 68515-51-5); Witamol 118 (Di-n-C8-C10-alkyl phthalate) (CAS No. 71662-46-9); Unimoll BB (CAS No. 85-68-7); Linplast 1012 BP (CAS No. 90193-92-3); Linplast 13XP (CAS No. 27253-26-5); Linplast 610P (CAS No. 68515-51-5); Linplast 68 FP (CAS No. 68648-93-1); Linplast 812 HP (CAS No. 70693-30-0); Palatinol AH (CAS No. 117-81-7); Palatinol 711 (CAS No. 68515-42-4); Palatinol 911 (CAS No. 68515-43-5); Palatinol 11 (CAS No. 3648-20-2); Palatinol Z (CAS No. 26761-40-0); Palatinol DIPP (CAS No. 84777-06-0); Jayflex 77 (CAS No. 71888-89-6); Palatinol 10 P (CAS No. 533-54-0); Vestinol AH (CAS No. 117-81-7).

It should be pointed out that the ring-hydrogenation of aromatic polycarboxylic acids or their esters can produce at least two stereoisomeric hydrogenation products from each isomer used. The quantitative proportions of the resultant stereoisomers with respect to one another depend on the catalyst used and on the hydrogenation conditions.

All of the hydrogenation products with any desired ratio(s) of the stereoisomers with respect to one another may be used without separation.

The present invention also provides the use of the alicyclic polycarboxylic esters of the invention as plasticizers in plastics. Preferred plastics are PVC, homo- and copolymers based on ethylene, on propylene, on butadiene, on vinyl acetate, on glycidyl acrylate, on glycidyl methacrylate, on acrylates, or on acrylates having, bonded to the oxygen atom of the ester group, alkyl radicals of branched or unbranched alcohols having from one to ten carbon atoms, or on styrene or on acrylonitrile, and homo- or copolymers of cyclic olefins.

The following plastics may be mentioned as representatives of the above groups:

polyacrylates having identical or different alkyl radicals having from 4 to 8 carbon atoms, bonded to the oxygen atom of the ester group, in particular having the n-butyl, n-hexyl, n-octyl, or 2-ethylhexyl radical, or isononyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers, and/or nitrocellulose.

The alicyclic polycarboxylic esters prepared according to the invention may moreover be used to modify plastics mixtures, for example the mixture of a polyolefin with a polyamide.

The present invention also provides mixtures made from plastics with the alicyclic polycarboxylic esters prepared according to the invention. Suitable plastics are the abovementioned compounds. These mixtures preferably comprise at least 5% by weight, particularly preferably from 20 to 80% by weight, very particularly preferably from 30 to 70% by weight, of the alicyclic polycarboxylic esters.

Mixtures made from plastics, in particular PVC, and comprising one or more alicyclic polycarboxylic esters prepared according to the invention, may be present in the following products, for example, or may be used for their production:

casings for electrical devices, such as kitchen appliances, computer cases, casings and components of phonographic and television equipment, of piping, of apparatus, of cables, of wire sheathing, of insulating tapes, of window profiles, in interior decoration, in vehicle construction and furniture construction, plastisols, in floor coverings, medical products, packaging for food or drink, gaskets, films, composite films, phonographic disks, synthetic leather, toys, containers for packaging, adhesive-tape films, clothing, coatings, and fibers for fabrics.

Besides the abovementioned applications, the alicyclic polycarboxylic esters prepared according to the invention may be used as a component in lubricating oil, or as a constituent of coolants or metalworking fluids. They can also be used as a component in paints, coatings, inks, and adhesives.

The examples below are intended to illustrate the invention without restricting the scope of application defined by description and the patent claims.

EXAMPLES

The examples below use catalysts which had been prepared from the support materials listed in Table 1 together with the physical data relevant to the invention.

TABLE 1

Properties of supports used

| Material | BET surface area in g/m$^2$ to DIN 66131 (N$_2$ adsorption) | Average pore diameter dp in nm to DIN 66133 (Hg porosimetry) | Total pore volume in ml/g | Proportion of pore volume made up by macropores in % | Proportion of pore volume made up by total of meso- and micropores in % | Producer or grade |
|---|---|---|---|---|---|---|
| A: TiO$_2$ | 48 | 34.2 | 0.46 | <5 | >95 | Degussa Aerolyst 7711 |
| B: ZrO$_2$ | 56 | 25.1 | 0.29 | >55 | <45 | Degussa H0907 |
| C: α-Al$_2$O non-inventive | 7 | 206.5 | 0.64 | >97 | <3 | Axence SP 512 |

The total pore volume was determined from the total of the pore volumes of pores with dp>7.6 nm (determined using Hg porosimetry) and pores with dp<7.6 nm (determined using the N$_2$ adsorption method).

Preparation of Hydrogenation Catalysts A, B and, C

To prepare hydrogenation catalysts based on the supports listed in Table 1, the supports were first dried at 80° C. After drying, the supports were impregnated or spray-dried with an aqueous ruthenium(III) nitrate solution which comprised a concentration of 0.8% by weight of ruthenium.

For the impregnation of the support, the Ru nitrate solution was diluted with water to a volume corresponding to the pore volume of the support.

The Ru solution was applied dropwise to the support material, or preferably by uniform spraying while the support is agitated. After drying at 120° C. under nitrogen, the ruthenium-salt-coated support was activated (reduced) for 6 hours in a hydrogen/nitrogen mixture (ratio 1:9) at 200° C.

Note: In the text below, the resultant catalysts have been indicated using the capital letters also used for the underlying support, the active metal and its content being given in appended brackets.

Hydrogenation Examples 1 to 5

The hydrogenation experiments were carried out in accordance with the following general specification:

90.7 g of the catalyst formed an initial charge in a catalyst basket and were carefully reduced in accordance with the above specification in the stream of hydrogen in a 1000 ml pressure reactor, and then treated with 590 g of liquid diisononyl phthalate (Vestinol 9, OXENO Olefinchemie GmbH). The DINP was hydrogenated using pure hydrogen. After hydrogenation of the starting material, the reactor was depressurized and the reaction mixture was analyzed by means of gas chromatography to determine its content of target product diisononyl cyclohexane-1,2-dicarboxylate (DINCH). This always showed the DINP conversion to be <99.9%.

The experimental conditions for the hydrogenation examples and the results of these have been entered in Table 2:

TABLE 2

DINP hydrogenation, hydrogenation examples

| Hydrogenation examples | Catalyst | Starting material | Pressure in bar | Temperature in ° C. | Reaction time in hours | Content of DINCH in % |
|---|---|---|---|---|---|---|
| 1 | A (1% Ru) | DINP | 200 | 80 | 3.5 | 99.4 |
| 2 | A (1% Ru) | DINP | 200 | 120 | 1 | 99.2 |
| 3 | A (1% Ru) | DINP | 50 | 120 | 2.5 | 99.3 |
| 4 | B (1% Ru) | DINP | 200 | 120 | 2 | 99.5 |
| 5 | C (1% Ru) | DINP | 200 | 80 | 20 | 99.4 |

Example 6

Hydrogenation of Monoisononyl Phthalate 444 g of phthalic anhydride (3 mol) and 432 g of isononanol (3 mol) (precursors of Vestinol 9) were slowly heated in a round-bottomed flask which has an internal thermometer and a stirrer, and on which a reflux condenser has been placed. A marked rise in temperature revealed the start of monoester formation at a temperature of 117° C. Immediately after the temperature rise began, the supply of heat was interrupted. After about 10 minutes the mixture was cooled, having by then reached its final temperature of about 150° C.

The composition which could be determined by gas chromatography was about 95% by weight of monoester, 3% by weight of diester, 0.5% by weight of isononanol, and 1.5% by weight of phthalic acid.

487 g (1.67 mmol, based on pure monoester) of this mixture were mixed, without further work-up, with 240 g (1.67 mol) of isononanol (precursor of Vestinol 9) and charged under nitrogen to a 1000 ml reactor. After addition of 70.7 g of catalyst A (1% Ru) the mixture was hydrogenated at 200 bar and 120° C., using hydrogen. Once the ring-hydrogenation of the aromatic carboxylic derivatives had ended, the reactor was depressurized. The reactor discharge was transferred into a standard esterification apparatus, mixed with a further 120 g (0.83 mol) of isononanol and about 0.07 g of tetrabutyl titanate, and esterified under standard conditions to give diisononyl cyclohexane-1,2-dicarboxylate (DINCH).

After removal of the excess alcohol by distillation, and after neutralization and work-up of the crude product by steam distillation, the purity of the DINCH obtained was 99.4%.

Example 7

Acid-Resistance of a Catalyst of the Invention

A saturated aqueous solution of phthalic acid was hydrogenated in the presence of catalyst A (1% Ru) at 100° C. and 100 bar to give 1,2-cyclohexanedicarboxylic acid. Once the hydrogenation had ended, the solution was discharged, and reactor and catalyst were flushed with methanol, isononanol, and DINP. DINP was then again hydrogenated under conditions analogous to Example 2. The hydrogenation was found to proceed with the same selectivities and with at least the same activity.

As can be seen from Table 2, catalysts A and B of the invention are clearly superior in activity to catalyst C.

What is claimed is:

1. A catalyst for the hydrogenation of aromatic compounds, which comprises at least one metal of the eighth transition group of the periodic table of the elements on or in a support material, wherein the support material has an average pore diameter of from 25 to 50 nm and a specific surface area greater than 30 $m^2/g$, and over 90% of the total pore volume of the support material is comprised of meso- and micropores with a diameter of 0.1 to 50 nm, and wherein the catalyst can hydrogenise the aromatic compounds to the corresponding alicyclic compounds.

2. The catalyst as claimed in claim 1, wherein the support material comprises activated carbon, silicon carbide, aluminum oxide, silicon oxide, aluminosilicate, titanium dioxide, zirconium dioxide, magnesium oxide, zinc oxide, or mixtures thereof.

3. The catalyst as claimed in claim 1, which further comprises at least one metal of the first transition group of the periodic table of the elements.

4. The catalyst as claimed in claim 1, which further comprises at least one metal of the seventh transition group of the periodic table of the elements.

5. The catalyst as claimed in claim 1, wherein the aromatic compound comprises benzene-, diphenyl-, naphthalene-, diphenyl oxide-, or anthracenecarboxylic acid, corresponding anhydrides, and/or corresponding esters.

6. The catalyst as claimed in claim 1, wherein the support material has an average pore diameter of from 25 to 40 nm.

7. The catalyst as claimed in claim 1, wherein the support material has a specific surface area of from 30-90 $m^2/g$.

8. The catalyst as claimed in claim 1, wherein the support material is comprised of meso- and micropores with a diameter of from 0.1 to 20 nm.

9. The catalyst as claimed in claim 1, wherein the content of the metal of the eighth transition group of the periodic table of the elements on or in a support material is from 0.1 to 30% by weight.

10. A process for the catalytic hydrogenation of an aromatic compound with one or more hydrogen-containing gases on a catalyst which comprises at least one metal of the eighth transition group of the periodic table of the elements on or in a support material, wherein the support material has an average pore diameter of from 25 to 50 nm and a specific surface area greater than 30 $m^2/g$, and wherein over 90% of the total pore volume of the support materials is comprised of meso- and micropores with a diameter of from 0.1 to 50 nm, the aromatic compounds comprise aromatic monocarboxylic acids or their alkyl esters or aromatic polycarboxylic acids or their anhydrides, half esters, or full esters, and said aromatic compounds are reacted to give the corresponding alicyclic poly- and/or monocarboxylic acid compounds.

11. The process as claimed in claim 10, wherein the support material comprises activated carbon, silicon carbide, aluminum oxide, silicon oxide, aluminosilicate, titanium dioxide, zirconium dioxide, magnesium oxide, zinc oxide, or mixtures thereof.

12. The process as claimed in claim 10, which further comprises at least one metal of the first transition group of the periodic table of the elements.

13. The process as claimed in claim 10, which further comprises at least one metal of the seventh transition group of the periodic table of the elements.

14. The process as claimed in claim 10, wherein the aromatic compound comprises benzene-, diphenyl-, naphthalene-, diphenyl oxide-, or anthracenecarboxylic acid, corresponding anhydrides, and/or corresponding esters.

15. The process as claimed in claim 14, wherein the alcohol components of the esters of the organic compounds are in each case identical or different and are alkoxyalkyl, cycloalkyl, and/or alkyl groups having from 1 to 25 carbon atoms, branched or unbranched.

16. The process as claimed in claim 10, wherein the support material has an average pore diameter of from 25 to 40 nm.

17. The process as claimed in claim 10, wherein the support material has a specific surface area of from 30-90 $m^2/g$.

18. The process as claimed in claim 10, wherein the support material is comprised of meso- and micropores with a diameter of from 0.1 to 20 nm.

19. The process as claimed in claim 10, wherein the content of the metal of the eighth transition group of the periodic table of the elements on or in a support material is from 0.1 to 30% by weight.

20. The process as claimed in claim 10, wherein the process is carried out in the pressure range 3 to 300 bar and the hydrogenation temperature of from 50 to 250° C.

* * * * *